United States Patent [19]
Pager et al.

[11] Patent Number: 5,520,637
[45] Date of Patent: May 28, 1996

[54] CLOSED-LOOP SYSTEM FOR INFUSING OXYTOCIN

[76] Inventors: David Pager, 941 Noio St., Honolulu, Hi. 96816; Robin J. Willcourt, 108 Green Ridge Dr., Reno, Nev. 89509

[21] Appl. No.: 381,496

[22] Filed: Jan. 31, 1995

[51] Int. Cl.[6] .................................................. A61M 31/00
[52] U.S. Cl. ................................................................ 604/66
[58] Field of Search ..................... 128/DIG. 12, DIG. 13; 604/890.1, 891.1, 892.1, 30, 31, 50, 246, 247, 65–67, 251–253

[56] References Cited

U.S. PATENT DOCUMENTS

| | | |
|---|---|---|
| 2,690,178 | 9/1954 | Bickford . |
| 2,925,814 | 2/1960 | Vibber et al. . |
| 4,078,562 | 3/1978 | Friedman . |
| 4,213,455 | 7/1980 | Ellson . |
| 4,280,494 | 7/1981 | Cosgrove, Jr. et al. . |
| 4,291,692 | 9/1981 | Bowman et al. . |
| 4,338,932 | 7/1982 | Georgi et al. . |
| 4,346,705 | 8/1982 | Pekkarinen et al. . |
| 4,364,386 | 12/1982 | Jenkins et al. . |
| 4,392,849 | 7/1983 | Petre et al. . |
| 4,409,966 | 10/1983 | Lambrecht et al. . |
| 4,468,219 | 8/1984 | George et al. . |
| 4,533,346 | 8/1985 | Cosgrove, Jr. et al. . |
| 4,551,133 | 11/1985 | Zegers de Beyl et al. . |
| 4,776,842 | 10/1988 | Franetzki et al. . |
| 4,871,351 | 10/1989 | Feingold . |
| 4,979,940 | 12/1990 | Bobo, Jr. et al. . |
| 5,100,380 | 3/1992 | Epstein et al. . |
| 5,116,312 | 5/1992 | Blankenship et al. . |
| 5,153,827 | 10/1992 | Coutre et al. . |
| 5,397,344 | 3/1995 | Garfield et al. ........................ 607/138 |

OTHER PUBLICATIONS

Wilcourt et al., "Induction of Labor . . . ", 170 Am. J. of Obstetrics and Gynecology No. 2 (Feb. 1992) 603–608.
Thorne et al., "The Relationship of the Maximum Amplitude . . . ", 19 IEEE Trans. on Biomedical Engineering (1972) 388–390.
Seitchik et al., "Intrauterine Pressure Wave–Form Characteristics . . . ", J. of Applied Physiology (1975) 443–448.

*Primary Examiner*—Corrine M. Maglione
*Assistant Examiner*—Manuel Mendez
*Attorney, Agent, or Firm*—James Creighton Wray

[57] ABSTRACT

An automatic, computer-controlled, closed-loop system administers pulsed doses of medication to patients. One application of the system is for administering oxytocin to women in labor. Once initial, preprogrammed doses of oxytocin are delivered, feedback signals from the patient are processed by a microcomputer. Those signals correspond to changing patterns of intrauterine contractions. In response to the feedback signals, the microcomputer controls the infusion of oxytocin by a pump and varies the size of the pulsed doses. The microcomputer also detects undesirable or emergency conditions from the signals, makes adjustments, and relates that information to the doctor. A display shows intrauterine pressure and relays information announcing the beginning and the end of contractions. The closed-loop system induces labor more efficiently than existing systems while using lower doses of oxytocin.

32 Claims, 3 Drawing Sheets

CLOSED-LOOP SYSTEM FOR INFUSING OXYTOCIN

BACKGROUND OF THE INVENTION

The present invention relates generally to automatic, responsive, computer-controlled systems for delivering pulsed medications to patients.

The basic idea of a closed-loop system for dispensing medication exists in biomedical systems. One such device, the Cardiff machine, implements a closed-loop system for dispensing oxytocin via continuous infusion. Oxytocin is a hormone used by physicians for controlling the process of labor stimulation and augmentation. Use of the Cardiff machine involves starting infusion at a low rate and progressively doubling that rate about every 15 minutes until a rate of 32 milliunits of oxytocin per minute is reached. Using a feedback mechanism, the infusion is suspended for 2.5 minutes after the onset of each contraction. If the contractions begin occurring at intervals of 2.5 minutes or less, the dose rate becomes constant.

Problems exist with that method of feedback control. First, because of the delay in the effect of oxytocin, the eventual rate produced is often too high. Second, since oxytocin stimulates the production of natural hormones having effects similar to those produced by oxytocin, varying or reducing the oxytocin infusion rates during labor may become necessary. Needs exist for medication delivery systems that have expedited responses to existing and developing medical conditions.

Efforts to improve the operational capabilities of closed-loop systems have proven unsuccessful. In one modified closed-loop system, the infusion rate is based on the average mark-space ratio exhibited by contractions, where a mark is considered to be occurring while the intrauterine pressure exceeds a certain value and a space is considered to be occurring otherwise. That feedback mechanism approach is ineffective because it makes no distinction between contractions of different strengths. Thus, that feedback mechanism treats the following in an identical way if the same mark-space ratio exists: (a) frequent, very strong contractions (e.g., ones whose peaks reach 75 mg Hg); (b) frequent contractions of moderate strengths (e.g., ones whose peaks reach 45 mg Hg); (c) frequent, very weak contractions (e.g., ones whose peaks do not reach 30 mg Hg). While case (b) may constitute satisfactory labor, case (a) may represent a case of hypertonus with danger of fetal distress which demands oxytocin administration to be reduced or suspended. Alternatively, case (c) may represent a condition in which the labor is not being significantly advanced, thus reducing fetal oxygen without receiving the benefits of accelerated labor. Needs exist for medication delivery systems that provide better and more accelerated mechanisms of feedback control.

Systems for providing medications of oxytocin in doses released in discrete intervals, rather than in a continuous manner, have proven inadequate. One system uses two fixed, but operator settable, time intervals, T1 and T2. T1 is the time period between doses of oxytocin and T2 is the duration of each dose. In that system, the pumping means is disabled in response to a contraction, the count for T1 is reset to zero in response to a contraction, and the size of the measured doses, as defined by time interval T2, is not altered by the system. In particular, T2 is not altered in response to the strength or frequency of contractions. Those results are too stringent and are undesirable. Needs exist for biomedical systems that administer dosed medications of oxytocin with size and frequency responsive to feedback signals.

Existing fetal monitoring systems use displays that show intrauterine pressure. Those displays are intended for the medical staff, and generally do not attract the interest or attention of the patient in labor. Needs exist for oxytocin delivery systems that have displays which are patient friendly and therapeutically relaxing.

SUMMARY OF THE INVENTION

This invention provides a completely automatic computer-controlled infusion pump for administering oxytocin to women in labor. The infusion is by means of timed pulses of oxytocin as opposed to the more usual methods having continuous infusion. The present invention performs with safety and efficiency equal or in excess of manually-controlled continuous infusion systems, while using only a fraction of the potent drug oxytocin. The timing of the oxytocin pulses in the present system is governed by the changing pattern of contractions. Information on contractions and the detection of various undesirable or emergency conditions is derived from the intrauterine pressure, which serves as an input to the controlling computer.

The closed-loop system includes an infusion pump, an oxytocin container and an expert system infusion pump controller that is responsive to intrauterine pressure. The controller is a microcomputer that initially converts from analog to digital the signal representing intrauterine pressure delivered from the strain gauge in the fetal monitor. Next, the microcomputer derives from the digital values necessary information for detecting emergency conditions. Finally, the microcomputer applies an algorithm for determining the timing and dose regime of oxytocin pulses on the basis of the pattern of past contractions and dose regimes already applied. A control signal is generated by the controller and delivered to the infusion pump. A display for informing the patient in real time when each contraction starts and ends is also incorporated.

The present invention makes use in the first instance of measured doses of oxytocin dispensed at discrete intervals of time that are varied in response to the strength and frequency of contractions. The controller assesses the adequacy of individual contractions based on the strength of the contractions. When the number of adequate contractions during a prescribed time interval is small, the controller increases the periodic doses of oxytocin from the infusion pump. Alternatively, when the number of adequate contractions in a prescribed interval is too large, the controller decreases the periodic dose. The system further assesses the effectiveness of individual contractions.

Maximum dosage levels are provided in the system. If the current periodic dose is at the maximum allowed level in dosage regimes where the pulse is being increased and the number of adequate contractions during a prescribed time period is small, or the number of non-trivial ineffective contractions is large, a regime of continuous infusion is triggered. The closed-loop system is sensitive to variations and fluctuations in physiological signals. The presence of medical contraindications can act to override suggested control signals. Oxytocin delivery is suspended or cancelled when a predetermined number of high-amplitude contractions occur in rapid succession, or when the intrauterine pressure exceeds a given value for a given time, or exceeds a given increment above the baseline tone for a given time, or remains unchanged for a given time.

By employing a superior feedback mechanism for controlling the infusion of oxytocin and by varying the size of the measured doses to dispense oxytocin, the present invention has operational characteristics superior to all existing systems. The automatic closed-loop oxytocin delivery system induces labor more effectively than other systems, producing shorter labors that are safer for both mother and child. The present invention also uses less oxytocin. That correlates into healthier children, as a close relationship has been demonstrated between the total dose of oxytocin received by a mother and the incidence of subsequent development of neonatal jaundice by the child. The pulsed method of administration leads to less receptor saturation and a more physiologic response, thereby reducing oxytocin-related complications, such as uterine hypertonus, fetal distress and neonatal hyperbilirubinemia. The computer-controlled method for administering pulsed oxytocin permits preprogrammed dose rates to be administered without the need for manual bolusing, which is time-consuming, tedious and inconsistent when used in a busy labor and delivery unit. Additional benefits recognized by the present invention include shorter labor durations and lower uterine resting pressures, thereby enhancing maternal comfort and increasing the safety of the child.

The display, when included in the present invention, clearly announces "contraction started" and "contraction ended" whenever those events occur. The assessment that a contraction has ended is made before the intrauterine pressure returns to its resting level. The timing of the announcement prompts patients to relax on the message "contraction ended", rather than when intrauterine pressure has fallen, thereby providing small but significant additional benefits to the mother and child.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
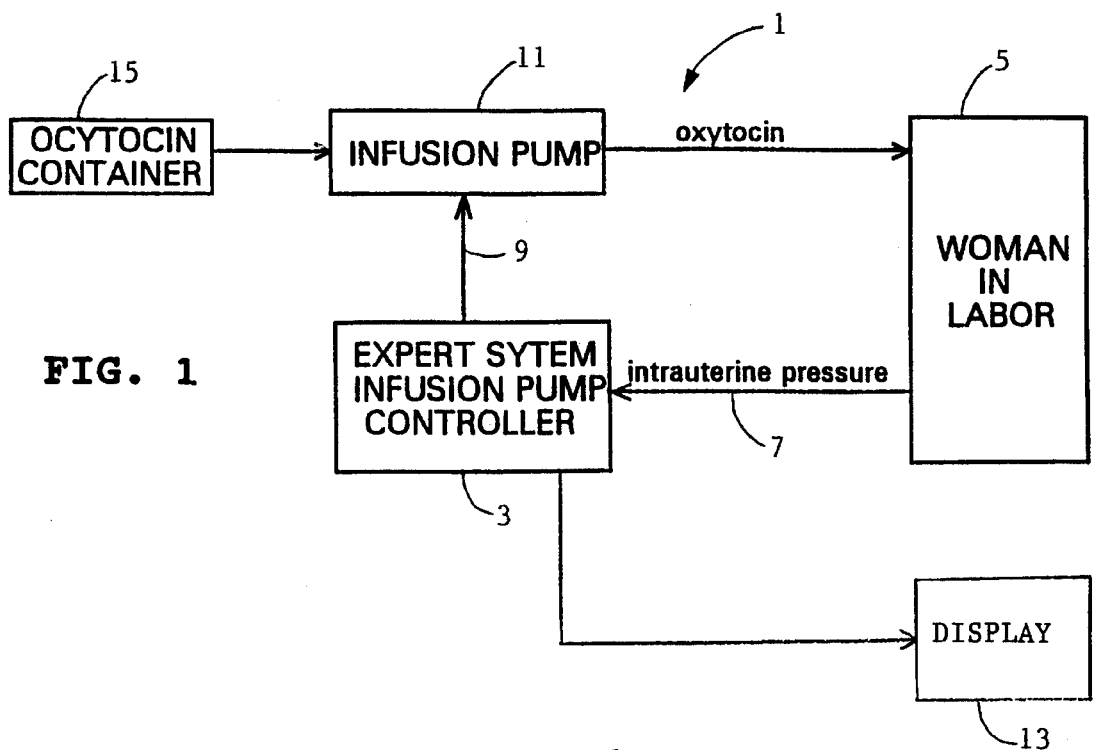
FIG. 1 is a schematic illustration of the automatic closed-loop infusion system.
Figure 2:
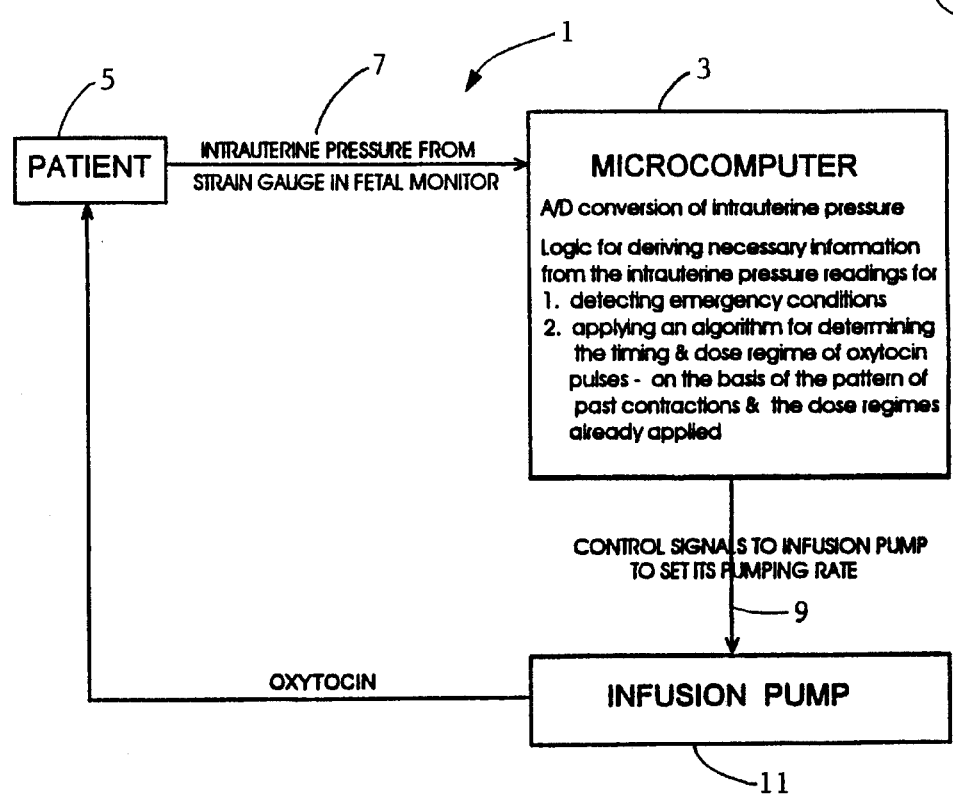
FIG. 2 is a schematic illustration of the present invention showing the main components and input and output signals.

Referring to the drawings and to FIGS. 1 and 2, a completely automatic computer-controlled infusion system 1 administers pulsed doses of medication. An expert system infusion pump controller 3, such as a microcomputer, receives an input signal from the patient 5. The controller 3 converts the analog input signal 7 to a digital signal, processes the digital signals and detects changing or emergency conditions. An algorithm is applied by the controller 3, and modified timing and dosage regime control signals 9 are generated. Those control signals 9 are delivered to an infusion pump 11 and set the pumping rate of the infusion pump 11. The infusion pump 11 administers pulsed doses of a drug from a medication container 15 according to the specifications of the control signal 9. A display system 13 is incorporated for delivering medical information to the patient 5 in real time.

A preferred embodiment of the present invention 1 is designed for controlling the infusion of a labor-inducing drug, such as oxytocin, into the bloodstream of a patient. The infusion is by means of timed pulses governed by changing patterns of contractions. Intrauterine pressure from a strain gauge in a fetal monitor is delivered, as an analog signal 7, to a controller 3. A monitor in the controller 3 converts the analog signal 7 to a digital signal. A computing means, governed by an algorithm, uses the digital signals to detect contractions and to measure the strength of the contractions. The computing means assesses the adequacy of individual contractions based on the strength of the contractions. If the number of adequate contractions during a predetermined time interval is too few, the control signal 9 delivered to the infusion pump 11 increases the periodic doses of the labor-inducing drug. If the number of adequate contractions during a predetermined interval is too many, a control signal 9 delivered to the infusion pump 11 decreases the periodic doses of the labor-inducing drug. The control signal 9 is regulated by the controller 3 so that the dose is not increased above a maximum level. Also, in the presence of medical contraindications, the control signal may be overridden by the controller 3 and ignored.

When the number of adequate contractions in a predetermined time interval is too small and the current periodic dose is at a maximum allowed level, a continuous infusion control signal 9 is delivered to the infusion pump 11. The continuous infusion rate is periodically increased if the number of adequate contractions in the preceding time interval has been too small. If the number of adequate contractions has been too high, the continuous infusion rate is decreased.

The computing means can further assess the effectiveness of individual contractions for advancing labor based on the strength of the contractions. If the number of non-trivial ineffective contractions during a predetermined time interval is too many, the signal 9 delivered to the infusion pump 11 decreases the periodic dose of the labor-inducing drug. If reducing the number of doses fails to remove the condition of excessively frequent non-trivial ineffective contractions, signals 9 are generated that increase the dosage, provided that the dose is not increased above a maximum level or in the presence of medical contraindications.

When the number of non-trivial ineffective contractions in a predetermined time interval is too many and the current periodic dose is at the maximum allowed level, a continuous infusion signal is delivered to the infusion pump 11. The continuous infusion rate is periodically increased if the number of ineffective transactions in the preceding time interval has been too few. The continuous infusion rate is decreased if the number of non-trivial ineffective contractions are too many.

Preferred embodiments of the present invention 1 measure the strength of the contractions by assessing the height of the intrauterine pressure level above a baseline tone level that occurred between the contractions in the preceding time period. The computing means further detects whenever three or more high-amplitude contractions occur in rapid succession. It also detects when the intrauterine pressure exceeds 22 mm Hg for over 90 seconds, or exceeds baseline tone+5 for over 2 minutes, or remains unchanged for over 2 minutes. When such conditions are detected, the infusion in progress is reduced or suspended and a warning indication is set on.

In one embodiment of the present invention, a feedback loop controls the rate of pulsing and the dose increments. The pulsed doses for the feedback responses range from 2 to 30 mU of oxytocin, to be administered no closer than 5 minutes apart and no sooner than 20 seconds after a contraction has reached baseline. The timing of the doses and the dosage size are determined by an algorithm receiving data from intrauterine pressure waveforms. In one embodiment, initial oxytocin doses measure two milliunits and are administered as a pulse over 2 seconds every 5 minutes for 10 minutes. If measured contractions are found inadequate, the dose is increased to 7 mU and is pulsed every 5 minutes, but no sooner than 20 seconds after a contraction reaches baseline. The dose is then increased by 5 mU every 40 minutes until the contractions are adequate. Once adequate contractions is established, the dose is held at the then existing rate.

The levels for adequate contractions and non-trivial ineffective contractions are predetermined and incorporated into the controller algorithm. In one embodiment, adequate contractions are considered to be those that are 35 mm Hg above the baseline and no more than 6 minutes apart from the previous contraction, and last at least 30 seconds above baseline tone+ 5, while non-trivial ineffective contractions are considered to be those that are less than 30 mm Hg above the baseline tone and no more than 2 minutes apart from the previous contraction and last at least 15 seconds above baseline tone+5 during which they exceed 20 mm Hg for at least 15 seconds.

The controller algorithm is also designed to release warning indications and to monitor doses when certain medical conditions arise.

The controlling computer 3 of the closed loop automatic infusion system 1 derives the necessary information from the intrauterine pressure input 7. That information includes the detection and classification of contractions, the continuously-updated evaluation of the resting baseline tone, and the detection of emergency conditions, such as excessively high intrauterine pressure, constant intrauterine pressure, and the occurrence of a series of contractions closely following each other whose amplitudes are all exceedingly high or exceedingly low. While eliciting that information, the controller 3 also must account for and correct inherent problems including noise involved in the acquisition of the intrauterine pressure due to strain gauge and A/D conversion, the changing baseline tone, the effects of maternal breathing, and artifacts in the pressure readings caused by coughing, sneezing and other patient movements.

Intrauterine pressure signals 7 from the patient 5 are received by the controller 3 from a strain gauge in the fetal monitor. The signals, which are delivered to the controller 3 as analog signals, are converted to a digital value. The variability in successive signals 7, due mainly to the mechanics of the strain gauge, is sufficient to affect the detection of new baseline tones and to give spurious indications of the potential onset of contractions. To eliminate the effects of that inherent noise, intrauterine pressure measurements are taken every 1/100 second and the average of the measurements over one second is evaluated. Those one second averages, referred to as readings, serve as the input to the subsequent decision tree for timing and dosage regimes.

To account for artifact noise due to coughing, sneezing and patient movement, the algorithm assumes that intrauterine pressure does not change more than 5 mm Hg in a second. A reading is determined to be legal if it is part of a set of 5 successive readings, none of which differs from its neighbors in the set by more than 5 mm Hg. If changes of more than 5 mm Hg are found, the reading is tagged as nonlegal. The data structures are circular buffers that store the last 60 readings, and a parallel buffer of flags specify the legality status of the corresponding reading.

Figure 3A:
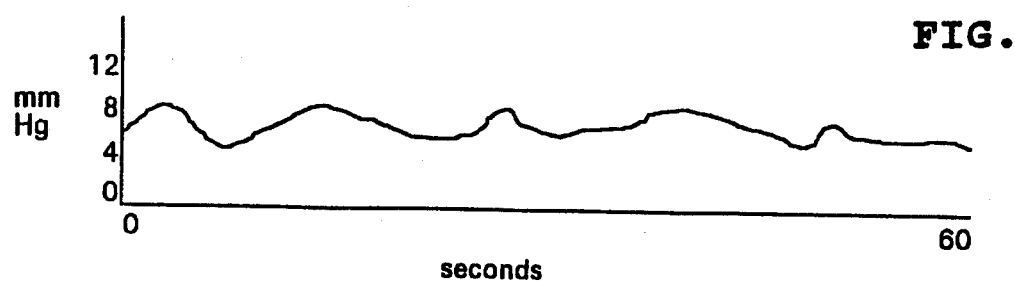
FIGS. 3A, 3B, 3C and 3D are graphical representations of intrauterine pressures over sixty second intervals.
Figure 3B:
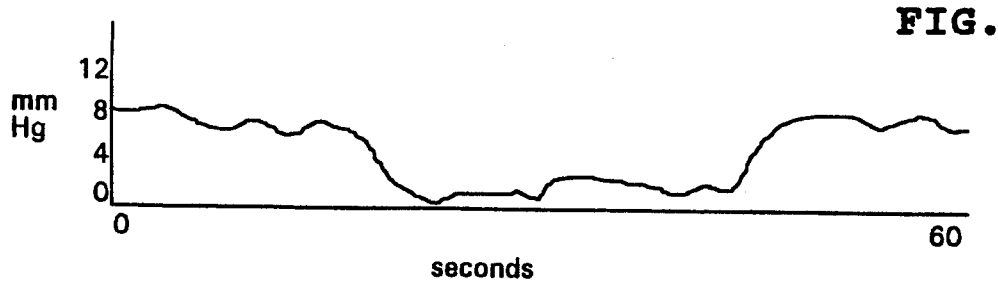
Figure 3C:
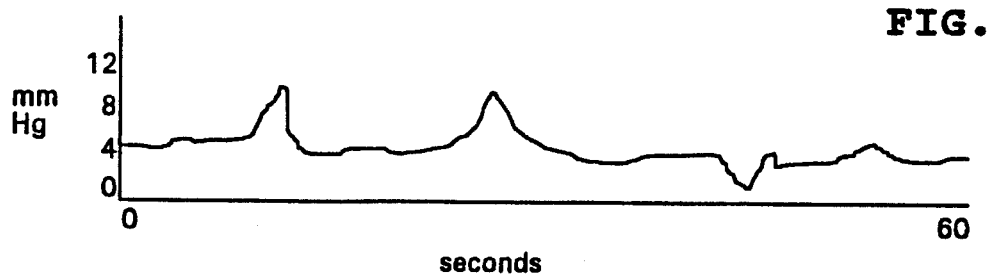

Since classifying contractions involves not merely the absolute value of the maximum pressure reached but also the excess of that value above the resting baseline tone, the resting baseline tone has to be continuously monitored. FIG. 3A represents a baseline tone since in the course of 60 seconds the intrauterine pressure does not change by more than 5 mm Hg. To determine a baseline tone value, the waveform must, over a 60 second interval, have at least 50 readings within a range of 5 mm Hg. FIG. 3B shows a waveform that is not accepted as a baseline by the algorithm, because less than 50 readings are within a range 5 mm Hg. FIG. 3C shows a waveform that is accepted by the algorithm, since only a few blips are not confined in the prevailing range of values. The readings within the 5 mm Hg range in this case would be averaged to determine the baseline tone value.

Figure 3D:
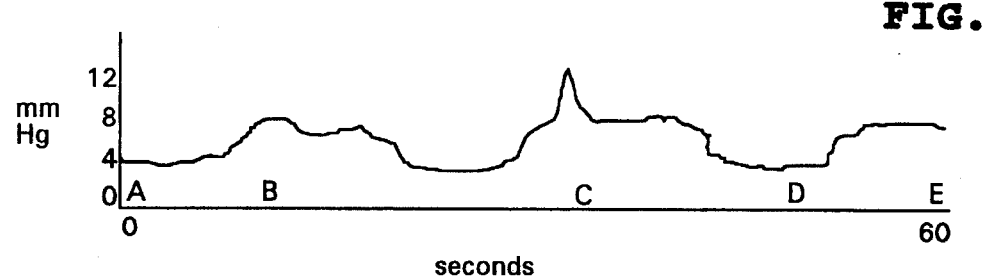

While the above determination of the baseline tone is adequate, the method does not unambiguously define a baseline tone in all cases. FIG. 3D is an example of a waveform where the above method does not correctly determine the baseline tone. In that case, the fifty readings between times A and D supply a different baseline tone from those between times B and E. It is not sufficient to simply take on average of the readings between A and B, since in this example the readings at C do not form part of the resting baseline tone. To correct for these situations, the algorithm is modified as follows. 20 mm Hg is taken as the largest possible baseline tone value. At that value, the 2 mm Hg ripple due to maternal breathing produces readings up to 22 mm Hg. For $1 \leq i \leq 22$, $T_i$ is the number of legal readings within the last 60 seconds that were of value i. The smallest value of i, $i_{min}$, and the largest value of $i_{max}$, are determined such that $$\sum_{j=i}^{i+4} T_j \geq 50$$

If no such values for $i_{min}$, $i_{max}$ exist, then no new baseline tone is defined by the 60 readings involved. Otherwise, let $\{x, \ldots, y\}$ be the intersection, listed in ascending order, of $\{i_{min}, i_{min}+1, {}_{min}+2, i_{min}+3, i_{min}+4\}$ and $\{i_{max}, i_{max}+1, i_{max}+2, i_{max}+3, i_{max}+4\}$. Next, let B be the average of the readings in $\{T_x, \ldots, T_y\}$, i.e., $$B = \sum_{j=x}^{y} T_j \times j/(y - x + 1)$$

Figure 4:
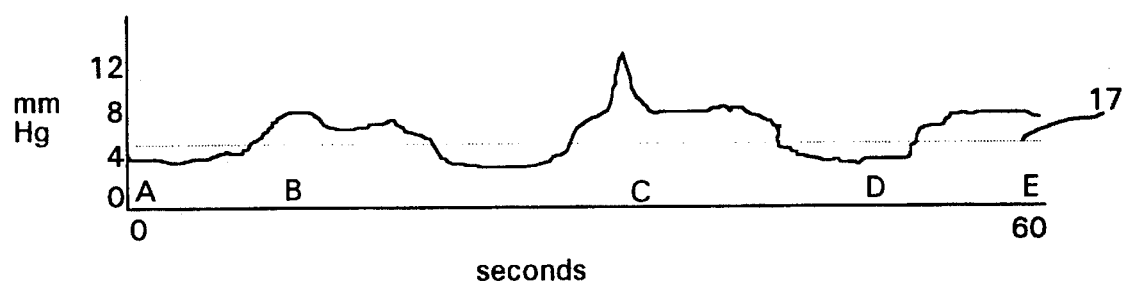
FIG. 4 is a graphical representation of the baseline tone determined from an algorithm using the input shown in FIG. 3D.

If B>20, then no baseline tone is defined. If $B \leq 20$, then B is the new baseline tone defined. FIG. 4 shows the application of that algorithm to the waveform of FIG. 3D to produce the baseline tone 17.

Contractions are provisionally detected whenever legal readings first reach a level of baseline tone+5, with the possible contraction lasting until the readings either drop below that value or define a new baseline tone. The waveform is taken to be an actual contraction if it lasts for at least 30 seconds or lasts at least 15 seconds during which it exceeds 20 mm Hg for at least 15 seconds. Even though some of the waveforms defined as contractions are not included in the categories of useful or harmful contractions, the determination that a contraction meeting the definition had in fact occurred is used in the timing of pulses to dispense oxytocin. The application of pulses is delayed, if necessary, until at least 20 seconds after a contraction has ended.

A contraction is classified as 1) adequate if it lasts at least 30 seconds, reaches a maximum amplitude>baseline tone+ 35, and occurs less than 6 minutes after the preceding contraction; 2) non-trivial ineffective if it lasts at least 15 seconds during which it exceeds 20 mm Hg for at least 15 seconds, reaches a maximum amplitude<baseline tone+30, and occurs less than 2 minutes after the preceding contraction; and 3) high frequency high amplitude if it reaches a maximum amplitude≧ baseline tone+30 and occurs less than 2 minutes after the preceding contraction.

The algorithms are also used to distinguish potential emergency conditions from the mimicking effects on the intrauterine pressure measurements due to inherent noise and patient activity. Potential emergency conditions detected by the present system include the occurrence of three or more successive high frequency high amplitude contractions, readings that exceed 22 mm Hg throughout the 90 seconds, and readings that exceed baseline tone+5 throughout the last two minutes, and readings that have remained unchanged throughout the last two minutes.

The present invention has a display for showing the intrauterine activities to the patient. The display clearly announces "contraction started" and "contraction ended" whenever those events occur. The assessment that a contraction has ended is made some time before the intrauterine pressure returns to its resting level. The patient display contributes to a sense of self knowledge and well being by the patient and reduces anxiety and unnecessary and unproductive patient stress.

While the invention has been described with reference to specific embodiments, modifications and variations of the invention may be constructed without departing from the scope of the invention, which is defined in the following claims.

We claim:

1. A closed-loop system for administering pulsed doses of medication to a patient comprising an infusion pump, connectable to the patient, a medication source connected to the infusion pump, and an expert system infusion pump controller connected to the patient and to the infusion pump for receiving a first analog signal from the patient, converting the first analog signal to first digital signals, converting a set of the first digital signals to a second digital signal, processing the second digital signal, generating a second control signal, and delivering the second control signal to the infusion pump for controlling a timing and dosage regime of medication infusion supplied from the medication source through the infusion pump to the patient.

2. The system of claim 1, further comprising a patient display connected to the infusion pump controller for delivering medical information to the patient in real time.

3. The system of claim 1, wherein the first analog signal is a pressure signal from a strain gauge in a monitor connected to the patient.

4. The system of claim 3, wherein the second digital signal is an average of the first digital signals taken from the patient over a short given interval of time.

5. The system of claim 1, wherein the infusion pump controller further comprises a converter for converting the first analog signal to the first digital signal, and a computer for assessing a patient's condition from the second digital signal and for generating the second control signal for controlling medication administration from the medication source to the patient by the infusion pump.

6. The system of claim 5, where the first analog signal is a pressure signal from a strain gauge in a monitor connected to the patient, and the computer comprises a processor for assessing, based on their strengths whether contractions are adequate contractions or are non-trivial ineffective contractions, and wherein the computer carries out a decision tree of timing and dose regimes in attempting to bring the frequency of adequate contractions within a given range, and to reduce the frequency of non-trivial ineffective contractions below a given limit.

7. The system of claim 5, wherein the first analog signal is a pressure signal from a strain gauge in a monitor connected to the patient, and the computer comprises a processor for determining whether contractions are adequate, or are non-trivial ineffective contractions, based on strength measurements of the contractions by measuring durations that second digital signals exceed given pressure levels, and exceed given increments above the baseline tone levels occurring between contractions in a preceding time period.

8. The system of claim 5, wherein the computer comprises a dosage control such that the second control signal generated by the computer instructs the infusion pump not to administer doses of medication above a maximum level.

9. The system of claim 1, wherein medication is oxytocin and the infusion pump delivers to the patient pulsed doses of oxytocin employing a range of pulse sizes that includes an upper limit, and enforces a first minimum period between doses, and a second minimum period after a contraction has ended before the application of a dose can commence.

10. The system of claim 1, wherein the controller detects and classifies contractions, continuously monitors and updates a resting baseline tone, and detects emergency conditions.

11. A method for administering pulsed doses of medication to a patient comprising receiving a first analog signal from a patient, converting the first analog signal to first digital signals, converting a set of the first digital signals to a second digital signal, processing the second digital signal, generating a second control signal, delivering the second control signal to an infusion pump, controlling a timing and dosage regime of medication infusion through the second control signal, and administering pulsed doses of medication to a patient based on instructions from the second control signal.

12. The method of claim 11, wherein the first analog signal is a pressure signal from a strain gauge in a monitor connected to the patient, further comprising a computer for assessing, based on their strengths whether contractions are adequate contractions or are non-trivial ineffective contractions, and wherein the computer carries out a decision tree of timing and dose regimes in attempting to bring the frequency of adequate contractions within a given range, and to reduce the frequency of non-trivial ineffective contractions below a given limit.

13. The method of claim 12, wherein the decision tree includes instructing the infusion pump to increase periodic doses of medication when a number of adequate contractions during a time interval is below a first limit, and instructing the infusion pump to decrease periodic doses of medication when the number of adequate contractions during the time interval is above a second limit.

14. The method of claim 13, further comprising defining adequate contractions as those that reach a given increment above the baseline tone level and occur less than a given maximum period after the previous contraction and which last for a given minimum amount of time.

15. The method of claim 13, wherein controlling the timing and dosage regime comprises instructing the infusion pump to administer continuous infusions of medication when the number of adequate contractions in the time interval is below the first limit and the dosage control indicates the doses of medication are at the maximum level.

16. The method of claim 12, wherein the decision tree includes instructing the infusion pump to decrease periodic doses of medication when the number of non-trivial ineffective contractions during a time interval is above a first limit.

17. The method of claim 16, wherein the decision tree further includes, for the case where applying the method of claim 16 has reduced the periodic doses below a minimum level and the number of non-trivial ineffective contractions during a time interval has remained above the first limit, instructing the infusion pump to increase periodic doses of medication when the number of non-trivial ineffective contractions during a time interval is above the first limit.

18. The method of claim 16, further comprising defining non-trivial ineffective contractions as those which last a given first minimum amount of time, during which they exceed a given pressure for a second minimum amount of time, but remain below a given increment above a baseline tone.

19. The method of 17, wherein the decision tree further comprises instructing the infusion pump to administer continuous infusions of medication when the number of non-trivial contractions in a time interval is above the first limit and the dosage control indicates the doses of medication are at a maximum level.

20. The method of claim 12, where the decision tree further comprises, when the current dosage regime is for continuous infusion, instructing the infusion pump to increase the infusion rate if the number of adequate contractions in a time interval is below a first limit and instructing the infusion pump to decrease the infusion rate if the number of adequate contractions in the time interval is above a second limit.

21. The method of claim 20, wherein the decision tree further comprises, when the number of inadequate contractions during the time interval is below the first limit and the infusion rate is at a maximum level, applying the method of claim 13.

22. The method of claim 12, wherein the decision tree further comprises, when the current dosage regime is for continuous infusion, applying the method of claim 13 when for a given number of time intervals, the number of non-trivial ineffective contractions has been above a given limit, and neither the number of such contractions nor a ratio of such contractions to a number of normal contractions in these time intervals has been declining.

23. The method of claim 11, wherein controlling the timing and dosage regime comprises instructing the infusion pump to administer pulsed doses of oxytocin employing a range of pulse sizes that includes an upper limit, and enforces a first minimum period between doses, and a second minimum period after a contraction has ended before the application of a dose can commence.

24. The method of claim 23, further comprising instructing the infusion pump to initially administer oxytocin in 2 mU boluses over 2 seconds every 5 minutes for 10 minutes, increasing levels to 7 mU if contractions are inadequate, and increasing dosage levels 5 mU every 40 minutes until the contractions are adequate.

25. The method of claim 11, wherein processing the second digital signal comprises detecting contractions, classifying the contractions, continuously monitoring and updating a resting baseline tone, and detecting emergency conditions.

26. The method of claim 25, further comprising accounting for artifact noise due to patient movement by only considering second digital signals that differ from other second digital signals from a predetermined set of neighbors by less than a given maximum increment.

27. The method of claim 25, wherein monitoring the baseline tone is by defining a new baseline tone only when a first minimum number of second digital signals collected over a time interval are within a second minimum range, and where the baseline tone is taken as the average of those second digital signals that are at a selected set of levels within the second minimum range.

28. The method of claim 25, further comprising generating a warning signal and delivering the warning signal to the infusion pump when at least a given number of successive contractions follow their predecessors within a given first interval of time and exceed a given first increment above the baseline tone.

29. The method of claim 25, further comprising generating a warning signal and delivering the warning signal to the infusion pump when second digital signals exceed a given first pressure level over a given time interval.

30. The method of claim 25, further comprising generating a warning signal and delivering the warning signal to the infusion pump when the second digital signals exceed a given first increment above the baseline tone over a given time interval.

31. A closed-loop system for administering pulsed doses of oxytocin to a patient comprising an infusion pump connectable to the patient, an oxytocin source connected to the infusion pump, an expert system infusion pump controller connected to the patient and to the infusion pump for receiving a first analog signal from the patient, the first analog signal being an intrauterine pressure signal, converting the first analog signal to first digital signals, converting a set the first digital signals to a second digital signal, processing the second digital signal, generating a second control signal, and delivering the second control signal to the infusion pump for controlling a timing and dosage regime of medication infusion supplied from the medication source through the infusion pump to the patient, and a patient display connected to the infusion pump controller for delivering medical information to the patient in real time and for announcing a start of the contraction and a conclusion of the contraction, the conclusion of the contraction announced at a time before pressure returns to a resting level.

32. An automatic closed-loop system for controlling infusion of a labor-inducing drug into a bloodstream of a patient, comprising a control for controlling an infusion rate, a monitor connected to the patient, a converter connected to the monitor for converting to a digital value an analog signal from the monitor determined by intrauterine pressure of the patient, a computer connected to the converter and to the control for inputting the digital value and for thereby detecting contractions, for measuring strengths of the contractions, for assessing adequacy of individual contractions based on the strengths of the contractions and for increasing the infusion rate of periodic doses of the labor-inducing drug which the control means dispenses if a number of adequate contractions in a preceding time interval has been too small, for decreasing the infusion rate of doses if the number of adequate contractions in the preceding time interval has been too large, and for preventing increasing of infusion rate above a maximum level or in the presence of medical contraindications.

\* \* \* \* \*